United States Patent [19]

Klehm

[11] Plant 4,247

[45] May 2, 1978

[54] PEONY PLANT NAMED CORAL CHARM

[75] Inventor: Roy G. Klehm, Barrington, Ill.

[73] Assignee: Klehm Boys Partnership, Arlington Heights, Ill.

[21] Appl. No.: 795,310

[22] Filed: May 9, 1977

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new peony plant variety particularly distinguished by the vibrant orange-coral color of its buds and newly opened flower petals which gradually changes as the blossom matures to become an unusual coral cream color when the petals begin to fall from the stem. This plant is an early blooming variety of medium height, with average quantity of foliage and a profuse production of medium sized semi-double flowers.

1 Drawing Figure

BACKGROUND OF THE NEW PLANT

My new variety of peony plant was discovered by me at Lombard, Ill., among a group of seedlings of (*lactiflora*) Minnie Shaylor × (*lobata*) Otto Froeber (both unpatented) resulting from a cross made by Samuel Wissing in the course of breeding efforts carried on since 1955 with the object of producing a plant combining the brilliant clear color of the species *lobata* with the strength and reliability of the species *lactiflora.* The color of this seedling attracted my attention and I promptly began propagation of this plant at Arlington Heights, Ill., by means of divisions and root cuttings. Successive generations of this new plant, produced by root division and root tip cuttings, have demonstrated that its distinctive features hold true from generation to generation and appear to be firmly fixed and this plant is now being grown for commercial exploitation at production farms at Barrington, Ill., and Champaign, Ill.

DESCRIPTION OF THE DRAWING

My new peony plant variety is illustrated by the accompanying full color photographic drawing which shows a full face view of the flower in full bloom, the colors shown being as nearly true as it is reasonably possible to obtain by conventional photographic procedures.

DESCRIPTION OF THE NEW PLANT

The following is a detailed description of the new peony variety with color specification according to the RHS Colour Chart, published by The Royal Horticultural Society of London, England, the observations having been made by me at Arlington Heights, Ill.

THE PLANT

Origin: Seedling.

Parentage:

*Seed Parent.*—Minnie Shaylor (unpatented).

*Pollen Parent.*—Otto Froeber (unpatented).

Classification: *Paeonia hybrida.*

Form: Bush.

Height: 28 inches (average).

Growth: Upright with medium strength, sturdy stems about 2/5 inch in diameter, and a typical growth rate for this genus.

Foliage: Average in quantity.

*Leaf size.*—7 to 8 inches long. Shape: Elliptically acute with smooth margins. Aspect: Glossy and smooth. Ribs and Veins: Pronounced. Petioles: About 1½ inches long.

*Leaflets.*—Three in number, about 4 inches long.

THE BUD

Size: Medium.

Form: Globular and smooth. Opening rate: Variable according to weather.

Color:

*When sepals first divide.*—Orange 29A.

*When petals begin to unfurl.*—Orange 28A.

Sepals: Hooded over bud and tightly wrapped.

*Color.*—Inside: Limpid Green 135D. Outside: Medium Green 135C.

Calyx:

*Shape.*—Polysepalous.

*Size.*—Broad.

*Aspect.*—Smooth.

*Splitting.*—None.

Peduncle: None.

THE FLOWER

Blooming habit: Annually — mid to late May.

Size of flower: Medium.

*Diameter.*—5 inches.

*Depth.*—2½ inches.

Borne: Singly.

Shape: Cup shaped when bloom first opens opening to semi-double as bloom matures.

Petalage: Number of petals: 38 to 40.

*Arrangement.*—Imbricated — semi-double.

*Form.*—Spoon shaped — concaved with smooth margins.

*Color.*—Inside and outside — varying with age from Persimmon Orange 28A through 28B to Marigold Orange 28C.

*Texture.*—Soft.

*Appearance.*—Satiny.

Petaloids: None.

Fragrance: Slight peony.

Disease resistance: Generally resistant to usual peony diseases, as observed at Northern Illinois growing grounds since 1961.

Persistence: Petals drop free.

Lasting quality:

*On plant.*—About 8 to 12 days.

*As cut flower.*—About 4 days.

REPRODUCTIVE ORGANS

Stamens:

*Number.*—More than 100.

*Arrangement.*—Evenly spread on outer margin of the calyx.

*Anthers.*—Length — 3/10 inch.

*Filaments.*—Length — 2/10 inch. Color: Golden Yellow.

*Pollen.*—Color: Golden Yellow.

Pistils: Number — 6.

*Styles.*—Length — ½ inch. Color: Silvery Green

*Stigmas.*—Color — Rosy Red.

The most distinctive characteristic of this new variety of peony plant is the lively coral-orange color of its buds and newly opened flowers and the gradually changing of the color to lighter tones as the flowers become exposed to ambient weather conditions reaching a coral cream shade at the time when the petals begin to fall off the stem.

This plant is a hardy early blooming variety, normally flowering about the middle of May of each year, and is particularly suited to cooler climates.

I claim:

1. A new and distinct variety of peony plant substantially as herein shown and described, characterized by the coral-orange coloration of its medium sized blossoms and its mid-May annual flowering habit.

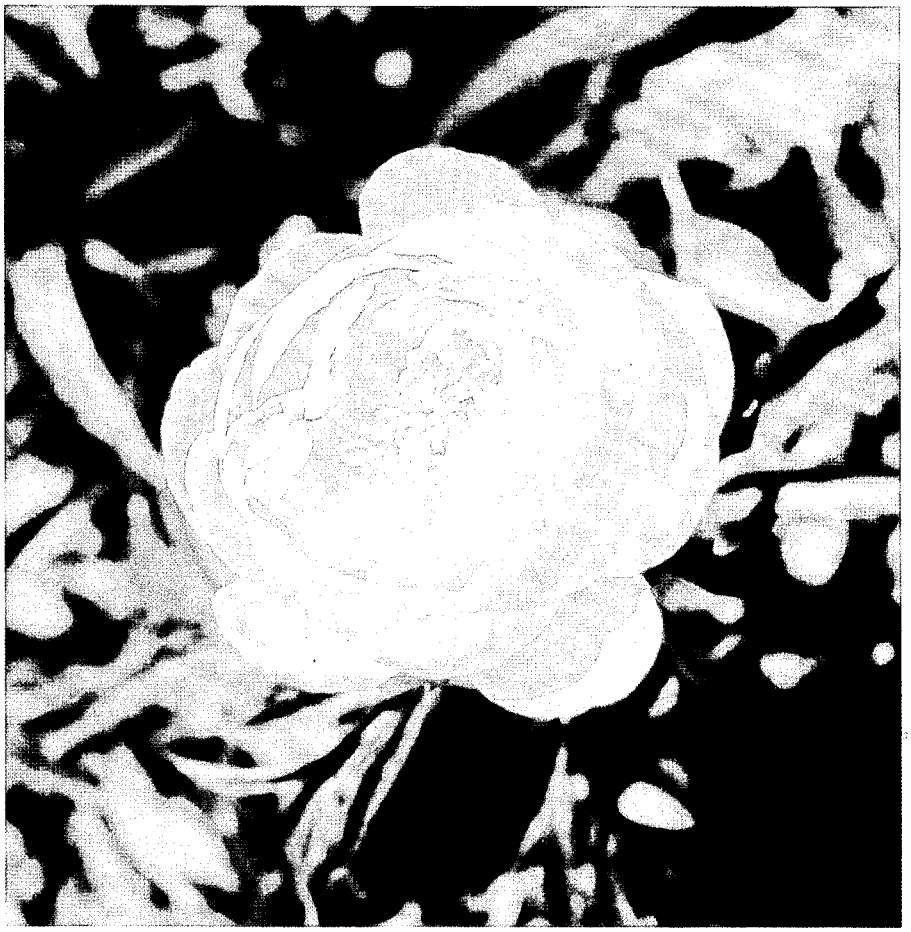

* * * * *